(12) United States Patent
Breuer et al.

(10) Patent No.: US 6,541,454 B1
(45) Date of Patent: *Apr. 1, 2003

(54) PHOSPHONATES, BIPHOSPHONATES AND PHARMACEUTICAL COMPOSITIONS CONTAINING THEM

(75) Inventors: Eli Breuer, Jerusalem (IL); Gershon Golomb, Efrat (IL); Gordon L. Amidon, Ann Arbor, MI (US); Ivan Sergeievitch Alferiev, Clementon, NJ (US); Naama El-Hanany Rozen, Rehovot (IL); Aviva Friedman-Ezra, Jerusalem (IL)

(73) Assignee: Yissum Research Development Company of the Hebrew University Jerusalem, Jerusalem (IL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/930,676

(22) PCT Filed: Apr. 3, 1996

(86) PCT No.: PCT/US96/04810

§ 371 (c)(1),
(2), (4) Date: Dec. 31, 1997

(87) PCT Pub. No.: WO96/31227

PCT Pub. Date: Oct. 10, 1996

(30) Foreign Application Priority Data

Apr. 4, 1995 (IL) .................................................. 113246

(51) Int. Cl.$^7$ .................................................. C07K 5/06
(52) U.S. Cl. .............................. 514/19; 514/7; 514/102; 514/108; 514/18; 530/331
(58) Field of Search .......................... 514/108, 7, 102, 514/18, 19; 530/331

(56) References Cited

U.S. PATENT DOCUMENTS 4,666,895 A * 5/1987 Bosies ........................ 514/108
4,830,847 A * 5/1989 Benedict ...................... 424/1.1

OTHER PUBLICATIONS

Ezra, J. Med. Chem. 43, 3641–3652, 2000.*
Cummings JAMA 280 (24) 2077–82, 1998.*
Cummings JAMA 280 (24) 2119, 1998.*
Mashiba BONE, 28 (5) 524–31, 2001.*
Sahota Osteoporosis International 11, 959, 2000.*
Siris Journal of Womens Health & Gender Based Medicine, 9 (6) 599–606, 2000.*
Niemi J. Med. Chem. 42, 5053, 1999.*
Beauchesne, Ann. Pharmacother 33, 587, 1999.*

* cited by examiner

Primary Examiner—Christopher S. F. Low
Assistant Examiner—David Lukton
(74) Attorney, Agent, or Firm—Eitan, Pearl, Latzer & Cohen-Zedek

(57) ABSTRACT

A method for treating patients having calcium related disorders includes using di- or tripeptide derivatives of bisphosphonates to enhance oral bioavailability of such compounds.

8 Claims, 3 Drawing Sheets

PHOSPHONATES, BIPHOSPHONATES AND PHARMACEUTICAL COMPOSITIONS CONTAINING THEM

BACKGROUND OF THE INVENTION

Calcium-related disorders in general and osteoporosis in particular are a major public health problem in developed countries. Several important pathological conditions are calcium-related and involve irregularities in calcium metabolism: Paget's disease, osteoporosis, hypercalcemia of malignancy, and osteolysis front bone metastases, etc. Bisphosphonates are a relatively new family of drugs used clinically in various calcium-related disorders including tumor osteolysis, and are undergoing clinical trials for osteoporosis. They are poorly absorbed following oral administration probably due to their high polarity and charge. IV and IM administration is a serious obstacle to their wide-spread use.

In the patent of Bosies et al. (U.S. Pat. No. 4,666,895 May 19, 1987) peptidyl diphosphonic acid derivatives are described. Bosies et al. Patent hypothesize that some peptidyl compounds will have better activity on bone: "In particular, they can be used in cases where the formation and breakdown of bone is disturbed, for example in cases of osteoporosis". Nothing is claimed, regarding the absorption of such compounds from the gastrointestinal tract following oral administration. The dosage recommended is much higher than that needed when effective oral absorption takes place. The dosage range recommended (see column 6) is from … "1 mg to 1000 mg, and preferably from 10 to 200 mg." Such doses are typical for non-absorbable bisphosphonates such as etidronate and pamidronate. The daily oral recommended dose of a recently approved bisphosphonate in the US, alendronate (Fosamax) is 10 mg and 40 mg, in the treatment of osteoporosis and Paget's disease, respectively (American Hospital Formulary Service AHFS Drug Information, section 92:00, 1995). As is known widely, this drug is 100 to 1000 times more effective than etidronate, the drug chosen by Bosies et al, for comparison. Typical absorption of such bisphosphonates in humans is in the range of 1%. Effective hydrolysis of the prodrug to the parent drug, for e.g., pamidronate or alendronate, is achieved following oral administration in the cytosol (intestinal cells). It is clear that if a peptidyl derivative of such a drug is administered to humans the dose should be reduced by 50 to 100 times, in order not to be lethal, due to the enhanced absorption of about 50 to 100 times of the prodrug. Bosies relates only to subcutaneous injections, in comparison to a first generation bisphosphonate, etidronate. Furthermore, selection of the peptidyl derivatives is not based on recognition by the transporter system nor on the possibility for hydrolysis to the parent drug. In their patent they seed a new compound, the administered drug being the active drug at the site of action (bone). The present invention relates specifically to the activity of the parent drug yielded form the prodrug following oral absorption.

The results are described ambiguously (+ and −system), and the activity of the compounds is compared to first generation bisphosphonate, etidronate (a non-nitrogen containing compound) rather than a more appropriate comparison to nitrogen-containing drugs such as pamidronate, known to be more effective (pamidronate and alendronate, nitrogen containing bisphosphonates, in clinical use are 10 to 1000 times more effective than etidronate. To the best of our knowledge no further development (since 1987) nor a scientific report is available for such compounds claimed by Bosies et al.

Bisphosphonates

Bisphosphonates have been approved for clinical use in Paget's disease, tumor osteolysis, and hypercalcemia of malignancy and approved in some countries for osteoporosis therapy. Most bisphosphonates are disodium salts of tie tetraacids (M.W. approximately 250), and are poorly absorbed from the GI tract (approximately 1% of the oral dose is absorbed). Chronic IM or SC administration of bisphosphonates causes irritation and necrosis, and the oral route has been associated with GI disturbances, resulting in poor patient compliance and side effects. For example, the treatment protocol of pamidronate in tumor osteolyis is 1-day slow and diluted IV infusion to avoid thrombophlebitis, but treatment is repeated if normocalcemia is not attained. Another example is the chronic therapy (years) required in osteoporosis.

Absorption Barriers

Clinically, the oral route is the most common and accepted one for delivering drugs of a low molecular weight, of up to 400–600. However, the low permeability of the intestinal epithelia towards highly polar and charged molecules impedes the effective absorption of many low molecular weight drugs. Many such drugs must be delivered parenterally by frequent injections. This is highly risky without close medical supervision. The problem is particularly acute in cases of drugs used for treatment of various chronic diseases such as cancer and age-related diseases, such as osteoporosis, which require prolonged drug treatment.

New Drugs for Calcium-related Disorders

Drugs require a degree of lipophilicity to pass through the GI barrier. In order to increase oral absorption of drugs with low membrane permeability, nonpolar prodrugs are often utilized. Due to the wide variety of esterases present in the target tissue for oral prodrug-regeneration, esters are the most common prodrugs when GI absorption is considered. Acyloxymethyl esters of bisphosphonic acids were proposed however this did not lead to a useful drug (European Patent EP 0 416 689 A2, date of filing Aug. 29, 1990). Similarly, Fels et al. proposed pharmaceutical compositions comprising bisphosphonates and sodium lauryl sulfate for increased oral absorption (U.S. Pat. No. 4,980,171, Dec. 25, 1990).

One way to increase membrane permeability of drugs is by utilization of the peptide carrier system (G. L. Amidon et al., *Absorption of difficult drug molecules: Carrier-mediated transport of peptides and peptide analogues,* Novel drug delivery and its therapeutic application, L. F. Prescott and W. S. Nimmo, Eds., John Wiley & Sons (1989) pp. 45–56).

SUMMARY OF INVENTION

The hypothesis of the present patent is completely different from the working hypothesis of Bosies et al. By carefully selecting specific di and/or tripeptide derivatives of bisphosphonates, enhanced oral bioavailability can be achieved due to the recognition by the active carrier transporter of the intestinal mucosae and the hydrolysis to the parent drug following oral administration.

Thus, the prodrug in our invention is a delivery system rather than a new compound for bone diseases. Therefore, the present selection of new compounds is based on enhanced absorption for the GI tract and hydrolysis to the parent compound resulting in improved oral, clinical treatment by a low dose. The selection of the di/tri-peptidyl moiety is based on transporter recognition and hydrolysis and not, as in Bosies et al patent, on resorbing activity on the bone.

Thus, the present invention relates to novel compounds of the general formula

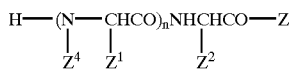

wherein Z is

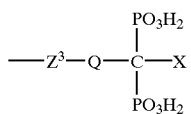

wherein $Z^1$ and $Z^2$ are independently a side chain of an amino acid or hydrogen, wherein $Z^4$ is hydrogen or $Z^4$ and $Z^1$ together with —N—CH—CO represent a proline residue.

where Q is

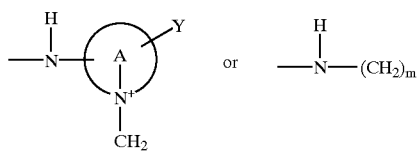

where $Z^3$ is a bond or a spacer group selected from NH, CO, NHCO, NHCO(CH$_2$)$_q$—CO, (CH$_2$)$_r$CO where r is zero or an integer, and where q is an integer or zero, m is 2, 3 or 4, n is greater than or equal to 0

X is —H or —OH,

Y is —H or —NR$^2$R$^3$, where A designates a 5- or 6-membered heterocyclic ring which contains 1, 2 or 3 nitrogen atoms, zero, 1 or 2 oxygen atoms and which may contain a sulfur atom, which contains up to and including 3 double bonds, where R$^2$ and R$^3$ are independently hydrogen, lower alkyl, lower alkenyl, lower alkoxy, (di) alkylaminoalkyl, alkoxyalkyl and where the ring A may be substituted by one or more conventional substituents, and to pharmaceutical compositions of improved absorption from the gastro-intestinal tract which contain as active ingredient an efficient quantity of a compound defined above.

Preferred compounds are of the formula

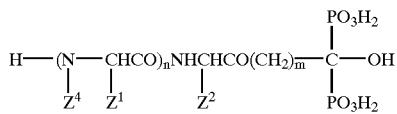

wherein n designates zero or an integer, m designates 2, 3 or 4; and where $Z^1$ and $Z^2$, which may be identical or different, each designates a side chain of an amino acid.

The compounds defined above are aminoacyl derivatives when n is zero, and they are peptidyl-bisphosphonates when n is an integer as defined above.

A wide range of amino acids can be used, and preferred ones for use in the peptidyl chain according to the invention are:

proline phenylalanine alanine lysine arginine aspartic acid glutamic acid

The invention furthermore relates to a method for the production of derivatives defined above, or their salts which comprises linking a desired bisphosphonate compound, of the Pamidronate or Alendronate type, to one or more amino acids.

The invention further relates to pharmaceutical compositions, for oral administration, which contain an effective quantity of a novel derivative defined above. The compositions according to the present invention are characterized by high absorption from the gastrointestinal tract.

The dosage in humans is dependent on various factors including drug potency, age, disease type and state, and the mode of administration. Since the present invention provides significantly enhanced oral absorption the dosage should be determined according to the extent of absorption of a specific peptidyl-bisphosphonate derivative. Therefore, the dose of the prodrug is typically about 20 to 100 times lower than the one usually prescribed for oral administration. One should also recall that the MW of a prodrug is higher than the active drug. The effective dosage range is form about 0.001 mg to about 100 mg per patient per day, a preferred range being of the order of about 0.02 mg to 1 mg per patient, per day in oral administration.

DETAILED DESCRIPTION OF THE INVENTION

In the following, the invention is described by way of illustration only with reference to representative examples. It ought to be clearly understood that the novel compounds can contain from one amino acid "elongation" and up to a multi-amino acid-residue peptidyl chain.

The novel compounds are effectively absorbed and after being absorbed, and due to enzymatic action, decomposed to provide the free active drug. It is preferred to use such peptidyl chains which are effective in balancing the negative charges of the bisphosphonates. It is possible that some of the novel conjugates are effective as such in the human body.

Peptidyl prodrugs of clinically approved bisphosphonates are effectively absorbed following oral administration. The present prodrug strategy was based on the rationale of neutralizing the negatively charged bisphosphonate molecule by a positively charged amino acid, and or at the same time making use of the peptide carrier system serving as a transporter for the prodrug.

Following membrane transport, the prodrug is subsequently hydrolyzed by a mucosal cell cytosolic enzyme such as prolidase, prolinase, dipeptidase, aminotripeptidase or possibly other hepatic/plasma enzymes, or is effective as such.

The rationale for the synthesis of peptidylbisphosphonates is twofold:

a) a peptidylbisphosphonate can be recognized by the nonspecific peptide transporter, and b) the free amino groups on the amino acid side chain are expected to neutralize partially or fully the phosphonate negative charges. Amino acids and peptides were linked to geminal-aminoalkylidenebisphosphonates (for example Pamidronate and Alendronate) by a simple chemical procedure to afford aminoacyl—and peptidylbisphosphonates. Aminoacyl or peptidyl bisphosphonates thus obtained are reconverted to the parent drug by enzymes or alternatively may be active as such in bone diseases. Synthesis of a representative example:

L-Prolyl-L-phenylalanylpamidronate (Pro-Phe-Pam,).

Experiments were also carried out with certain compounds according to the invention, having a heterocylclic ring in the molecule.

Results similar to the ones demonstrated above and in the Figure were obtained with these.

Figure 1A:
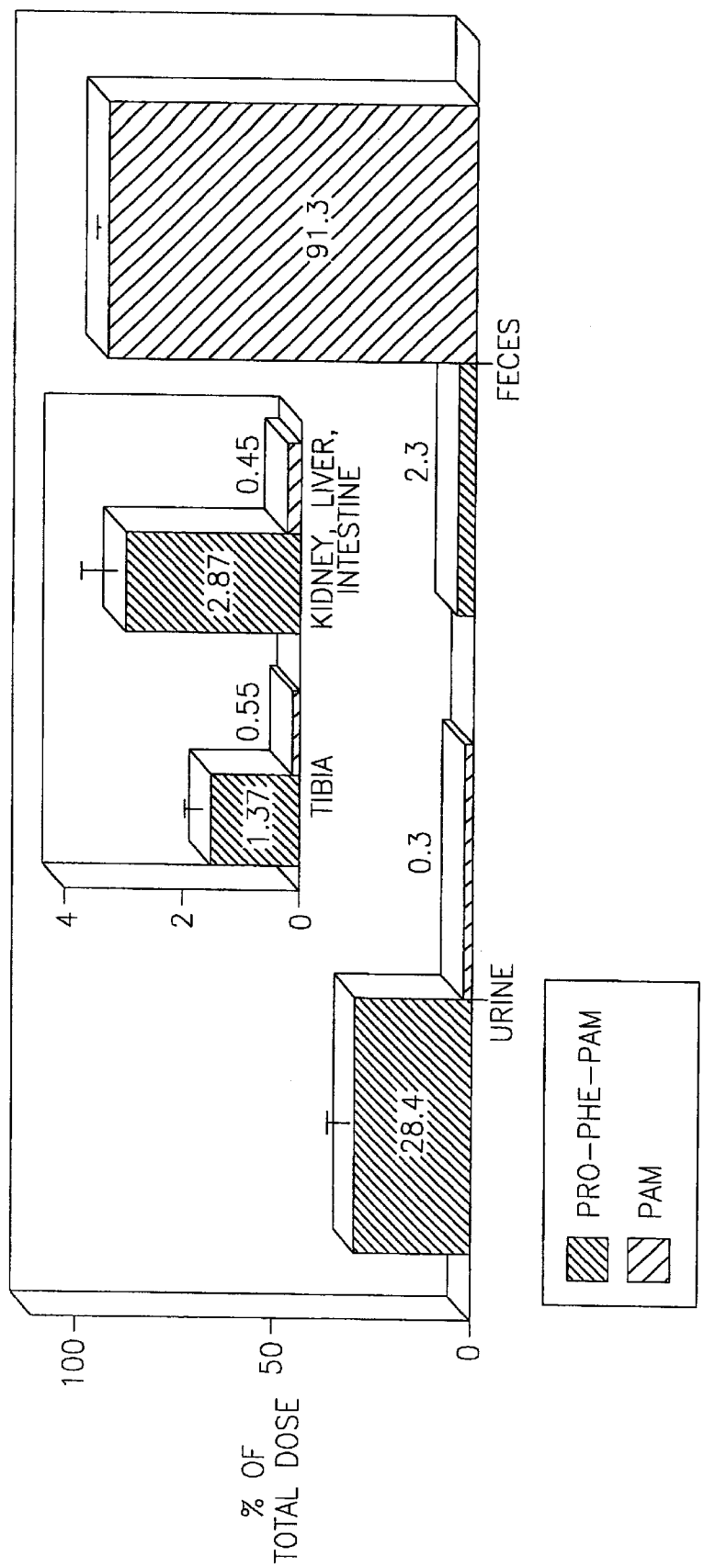
FIGS. 1A–1C show the absorption of orally administered Pro-Phe-Pam in various organs.
Figure 1B:
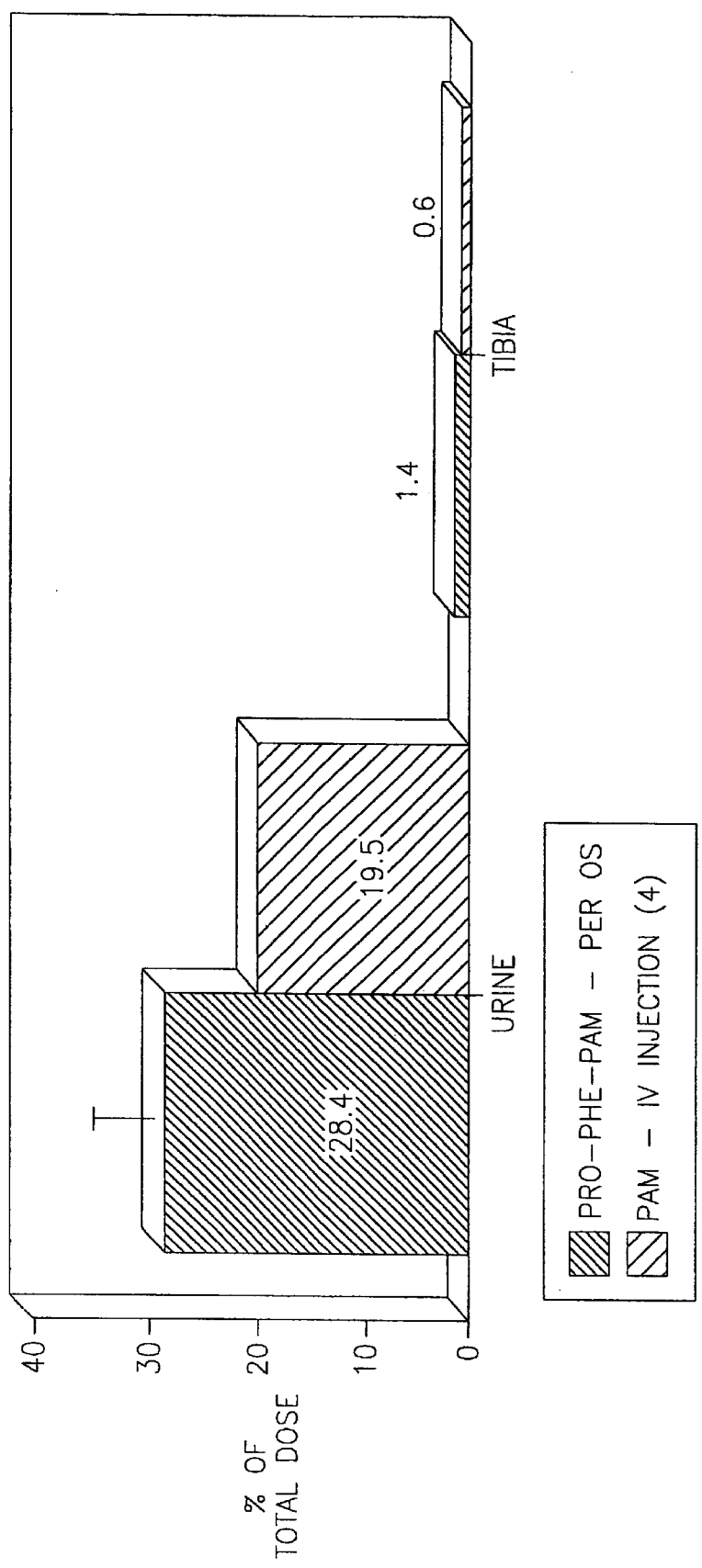
Figure 1C:
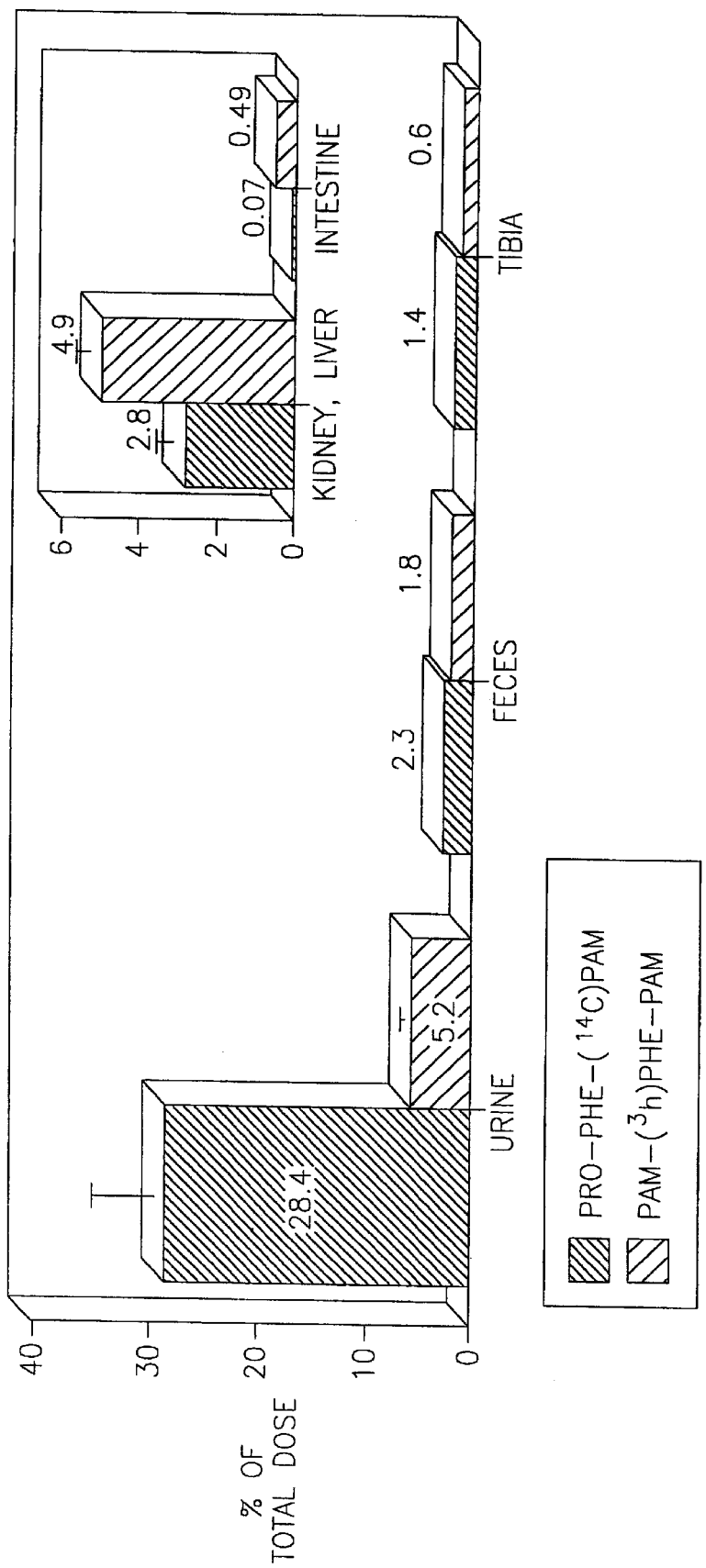

FIGS. 1A–1C relate to the concentration of Phe-Pamidronate and Pamidronate in various organs 24 hours after Peroral Administration in rats, (Pro-($^3$H)Phe-($^{14}$C) Pam, ($^{14}$C) Pam, 10 mg/kg. The scale indicates % of total dose.

"1" related to tibia, "2" relates to kidney, liver, intestine, "3" relates to kidney and liver.

"4": F. Wingen and D. Schmahl, Arzneim. Forschung 37, 1037–1042 (1989).

What is claimed is:

1. A compound represented by the structure having the following formulation:

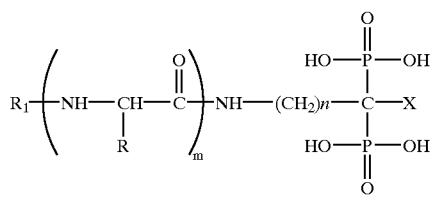

on a salt thereof
wherein

X=H, OH n is an integer of 2 or 3 m is an integer of 2 or 3

R is the side chain of a naturally-occurring amino acid, and

R1 is H, or R and R1 together with the NH—CH to which they are bonded represent the pyrollidine group of proline.

2. A compound represented by the structure having the following formulation:

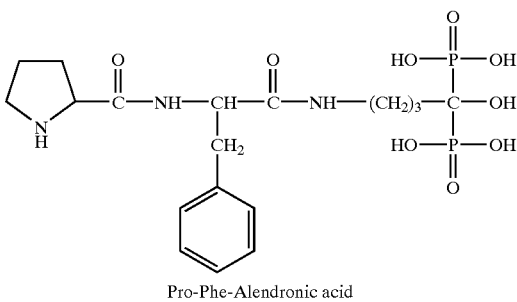

Pro-Phe-Alendronic acid on a salt thereof.

3. A compound represented by the structure having the following formulation:

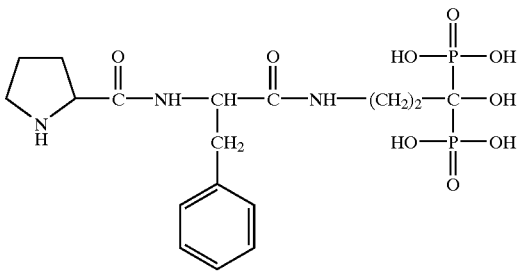

Pro-Phe-Pamidronic acid on a salt thereof.

4. A composition comprising the compound of claim 2, and a pharmaceutically acceptable carrier.

5. A pharmaceutical composition comprising the compound of claim 3, and a pharmaceutically acceptable carrier.

6. A composition comprising the compound of claim 1, and a pharmaceutically acceptable carrier.

7. A method of increasing the oral bioavailability of an aminoalkylidene bisphosphonate of the formula

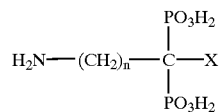

comprising (a) coupling the aminoalkylidene bisphosphonate to a dipeptide or tripeptide to form a compound according to claim 1, and (b) administering the compound according to claim 1 to a subject in need thereof, for a time and under conditions effective to achieve release of the aminoalkylidene bisphosphonate from said compound.

8. A method of inhibiting bone resorption comprising administering a compound according to claim 1 to a subject in need thereof, for a time and under conditions effective to achieve release of the aminoalkylidene bisphosphonate [H$_2$N—(CH$_2$)$_n$—C(X)(PO$_3$H$_2$)$_2$] from said compound.

* * * * *